US005658893A

United States Patent [19]
Anderson et al.

[11] Patent Number: 5,658,893
[45] Date of Patent: Aug. 19, 1997

[54] METHOD FOR INHIBITION OF ROTAVIRUS INFECTION WITH CARRAGEENAN

[75] Inventors: Steven Neal Anderson; Joseph Paul Schaller, both of Columbus; Terrence Bruce Mazer, Reynoldsburg; Stephen John Kirchner, Westerville, all of Ohio

[73] Assignee: Abbott Laboratories, Abbott Park, Ill.

[21] Appl. No.: 412,808

[22] Filed: Mar. 29, 1995

[51] Int. Cl.⁶ .................................................. A61K 31/715
[52] U.S. Cl. .............................. 514/54; 514/59; 536/114; 536/118; 536/122; 536/123.1
[58] Field of Search ................................ 514/12, 54, 56, 514/59

[56] References Cited

U.S. PATENT DOCUMENTS 5,288,704  2/1994  Ungheri et al. .......................... 514/12

FOREIGN PATENT DOCUMENTS

| 293826 | 12/1988 | European Pat. Off. | A61K 31/725 |
| 2262531 | 6/1993 | United Kingdom | A61K 31/725 |
| WO8806396 | 9/1988 | WIPO . | |
| WO 94/04136 | 3/1994 | WIPO . | |
| WO9415624 | 7/1994 | WIPO | A61K 31/725 |

OTHER PUBLICATIONS

Superti, et al., "Effect of polyions on the infectivity of SA-11 rotavirus in LCC-MK2 cells," Comp. Immun. Microbiol. Infect. Dis., vol. 16; No. 1, 1993, pp. 55–62.

Murray et al., "Medical Microbiology", Mosby, 1994, pp. 62 and 63.

Yolken et al., "Human Milk Mucen Inhibits Rotavirus Replication and Prevents Experimental Gastroenteritis", Journal of Clinical Investigation 90, 1984–1991, (1992).

Hoshino et al., "Rotavirus Vaccine Development for the Prevention of Severe Diarrhia in Infants and Young Children", Trends in Microbiology 2:242–249, (1994).

DeClerq, "Antiviral Agents: Characteristic Activity Spectrum Depending on the Molecular Target with Which They Interact", Advances in Virus Research 42:2, (1993).

DeClerq, "Selective Virus Inhibitors", Microbiologice 13:165–178, (1990).

Gonzalez et al., "Polysaccharides as Antiviral Agents: Antiviral Activity of Carrageenan", Antimicrobial Agents and Chemotherapy 31(9):1388–1393 (1987).

Mizumoto et al., "Sulfated Homopolysaccharides with Immuno-Modulating Activities are More Potent Anti-HTLV-III Agents Than Sulfated Heteropolysaccharides", Japanese Journal of Experimental Medicine 58(3):145–151, (1988).

Nakashima et al., "Purification and Characterization of an Avian Myeloblastosis and Human Immunodeficiency Virus Reverse Trranscriptase Inhibitor, Sulfated Polysaccharides Extracted from Sea Algae", Antimicrobial Agents and Chemotherapy 31(10):1524–1528, (1987).

Girond et al., "Antiviral Activity of Carrageenan on Hepatities A Virus Replication in Cell Culture", Research in Virology 142:261–270, (1991).

Gerna et al., "Immunoperoxidase Techniques for Rapid Human Cytomegalovirus Identification", Archives on Virology 50:311–321 (1984).

Kitamoto et al., "Comparative Growth of Different Rotavirus Strains in Differentiated Cells (MA 104, HerG2, and CaCo–2)" Virology 184:729–737 (1991).

*Primary Examiner*—James O. Wilson
*Attorney, Agent, or Firm*—L. R. Drayer; T. D. Brainard; D. O. Nickey

[57] ABSTRACT

A method is provided for inhibiting rotavirus infection of human cells by treating the rotavirus with a carrageenan. The most effective agent in inhibiting cellular rotavirus infection is lambda-carrageenan, which may be formulated in a liquid and ingested enterally. A composition containing lambda-carrageenan is an aspect of the invention.

7 Claims, 1 Drawing Sheet

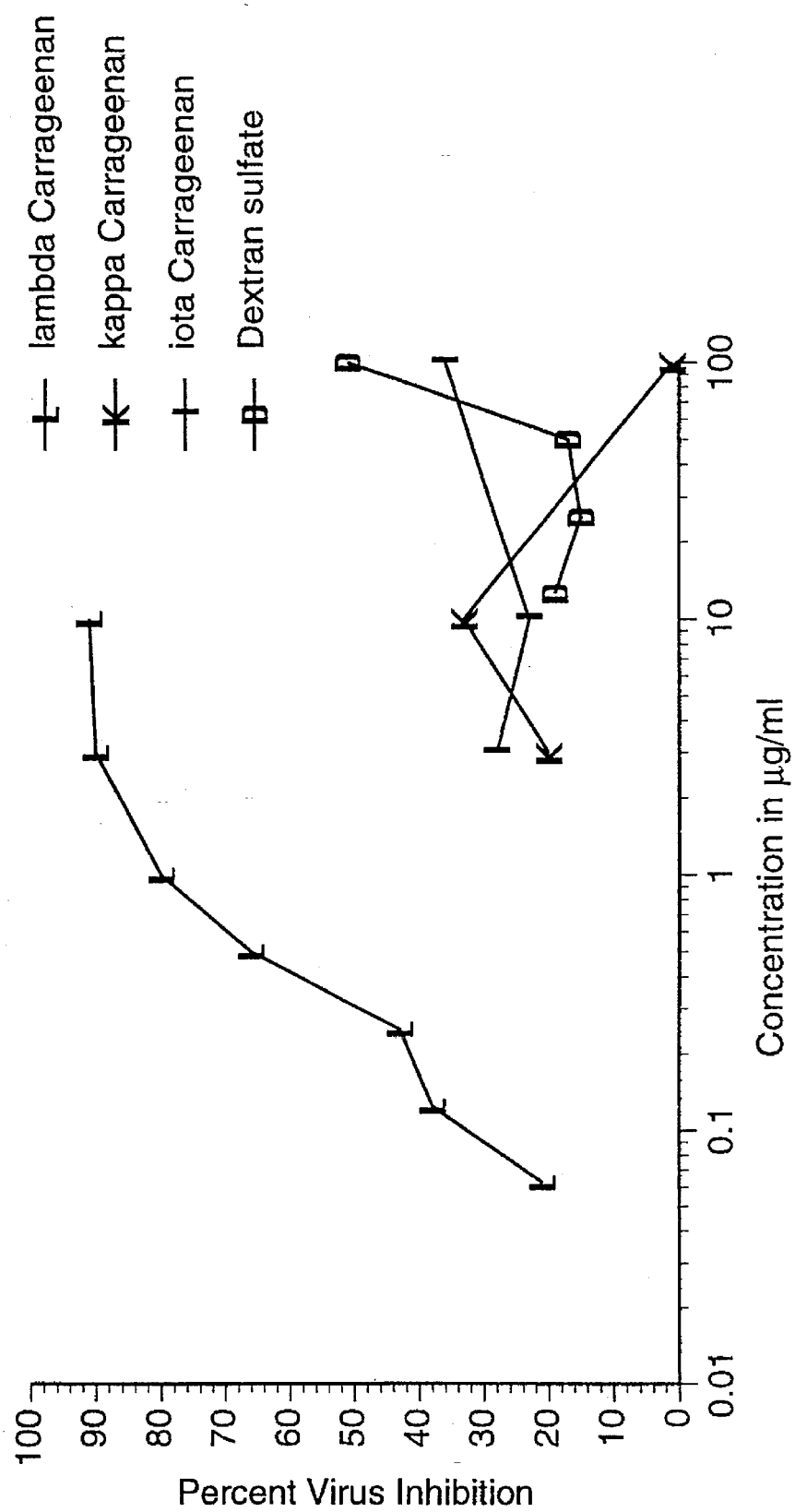

METHOD FOR INHIBITION OF ROTAVIRUS INFECTION WITH CARRAGEENAN

FIELD OF THE INVENTION

The present invention relates to the use of carrageenan to inhibit infection of animal cells by rotavirus. More particularly, the invention relates to the use of lambda carrageenan to inhibit infection of animal cells by human rotavirus.

BACKGROUND OF THE INVENTION

Rotaviruses are the most important viral agents causing gastroenteritis in children living in both developing and developed countries (Yolken et al, "Human Milk Mucin Inhibits Rotavirus Replication and Prevents Experimental Gastroenteritis", *Journal of Clinical Investigation* 90, 1984–1991, 1992). Rotaviruses also cause diarrhea in nursing homes and day care centers, among travelers, in adults who have contact with children, and in immunocompromised patients.

Rotaviruses cause 35–50% of severe diarrheal episodes in infants and young children in both developed and developing countries, and are the most important etiological agents of severe diarrhea in this age group. Rotaviruses infect over 90% of humans by age 3 in both developed and developing countries regardless of hygiene standards. In developing countries rotaviruses are estimated to cause 18 million cases of moderately severe or severe diarrhea and over 870,000 deaths annually in infants and young children under 5 years old (Hoshino et al., "Rotavirus Vaccine Development for the Prevention of Severe Diarrhea in Infants and Young Children", *Trends in Microbiology* 2:242–9, 1994). Thus, there is an urgent need to develop methods of preventing infection of humans, especially infants, from the consequences of infection by rotavirus.

Rotaviruses are included among the Reoviridae. They are nonenveloped viruses with an icosahedral morphology and a double-layered protein capsid containing 11 segments of a double-stranded ribonucleic acid (RNA) genome. The viruses are stable over wide pH and temperature ranges and in airborne aerosols. The virion (virus particle) delivers the nucleocapsid core through the acidic environment of the gastrointestinal tract and across the intestinal lumen to the target tissue. The complete virion is partially digested in the G.I. tract and the viruses are adsorbed to columnar epithelial cells that cover the villi of the small intestine. Upon entry into the cell, the outer capsid releases the core into the cytoplasm, and the enzymes in the core initiate mRNA production. The virus causes permeability changes and cell lysis. Rotaviruses are assumed to be passed from person to person by the fecal-oral route and the virus survives on hands and on inanimate objects.

It is known that sulfated polysaccharides specifically interfere with the adsorption process of enveloped viruses (De Clerq, "Antiviral Agents:Characteristic Activity Spectrum Depending on the Molecular Target with Which They Interact", *Advances in Virus Research* 42:p.2, 1993; De Clerq, "Selective Virus Inhibitors", *Microbiologica* 13:165–178, 1990). The group of sulfated polysaccharides contains a number of compounds including dextran sulfate and iota- (ι-), kappa- (κ-), and lambda- (λ-) carrageenans. The antiviral activity of dextran sulfate and carrageenans has been previously demonstrated against particular viruses. De Clerq in the 1993 review article refers (p.9) to a variety of enveloped viruses including retroviruses, herpesviruses, poxviruses, togaviruses, paramyxoviruses, and rhabdoviruses whose replication is inhibited by these sulfated polysaccharides. De Clerq, however, claims, contrary to the disclosure of the instant invention, that nonenveloped viruses, included reoviruses, are insensitive to inhibition by the sulfated polysaccharides.

The inhibitory property of sulfated polysaccharides, including the carrageenans, against various viruses has been described in the relevant literature. Gonzalez et al. ("Polysaccharides as Antiviral Agents: Antiviral Activity of Carrageenan", *Antimicrobial Agents and Chemotherapy* 31(9):1388–1393, 1987) found that iota-carrageenan showed strong antiviral activity against herpes simplex virus type I (HSV-1). Contrary to the results reported in De Clerq (1993) that sulfated polysaccharides inhibit virus attachment to the cell surface, Gonzalez et al. found, using labeled virion particles, that HSV-1 virions are internalized even in the presence of high concentrations of iota-carrageenan. This suggests that, at least for HSV-1, carrageenan inhibits a step in virus replication subsequent to viral attachment and internalization.

Sulfated homopolysaccharides, including cellulose sulfate, dextran sulfate and carrageenans, were shown by Mizumoto et al. ("Sulfated Homopolysaccharides with Immunomodulating Activities are More Potent Anti-HTLV-III Agents than Sulfated Heteropolysaccharides", *Japanese Journal of Experimental Medicine* 58(3): 145–151, 1988) to inhibit the growth of human T cell lymphotropic virus type III. Nakashima et al. ("Purification and Characterization of an Avian Myeloblastosis and Human Immunodeficiency Virus Reverse Transcriptase Inhibitor, Sulfated Polysaccharides Extracted from Sea Algae", *Antimicrobial Agents and Chemotherapy* 31(10):1524–1528, 1987) described a member of the lambda carrageenan family that had an inhibitory effect on reverse transcriptase activity of Human Immunodeficiency Virus (HIV) and suppressed replication of the virus in vitro. Girond et al. ("Antiviral activity of carrageenan on hepatitis A virus replication in cell culture", *Research in Virology* 142: 261–270, 1991) found that sulphated polysaccharides such as iota-, kappa-, and lambda-carrageenan showed a potent inhibitory effect on the replication of hepatitis A virus (HAV), a non-enveloped virus, in a human hepatoma cell line. Iota- and lambda-carrageenan were shown to be especially effective at inhibiting HAV antigen expression and infectivity.

WO 94/15624 discloses the use of sulphated polysaccharides, including carrageenan and dextran sulfate, to inhibit the transmission of HIV, the causative agent of AIDS. WO 88/06396 discloses a method for treating retroviral infections, including infection with the AIDS virus, by administering a carrageenan or a mixture of carrageenans. In EPA 293,826 sulfated polysaccharides, including dextran sulfate and carrageenans, are disclosed as in vitro inhibitors of HIV-1. GB 2,262,531 A disclosed that sulphated polysaccharides produced by a class of marine algae showed antiviral activity against both DNA and RNA viruses including the retroviruses and particularly against HIV.

In view of the different responses by different viruses to sulfated polysaccharides described above, it is clear that the response of a particular virus to carrageenan cannot be predicted with certainty without experimentation. The mechanism by which sulfated polysaccharides, particularly the carrageenans, inhibit viral replication and infectivity may not be uniform as different investigators reported contradictory findings when working with different viruses and cells types. It would not be obvious to one skilled in the art that a substance such as a sulfated polysaccharide that is an effective inhibitor of one virus would demonstrate similar efficacy against another virus. None of the cited references disclosed the use of carrageenans or other sulfated polysaccharides to inhibit infection of animal cells with rotavirus. The preferred sulfated polysaccharides of the present invention are the carrageenans or dextran sulfate, with the most preferred being lambda-carrageenan. Lambda-carrageen was shown in experiments to be described below to be the most efficacious in inhibiting rotavirus infection in vitro.

The prevalence of rotavirus infection in groups at risk, especially infants and children, and the seriousness of its effects attest to the need for developing effective treatments. The present invention demonstrates that carrageenan, and particularly λ-carrageenan, is an effective inhibitor of rotavirus infection in animal cells. Animal studies are being conducted to further evaluate the efficacy of λ-carrageenan in the treatment of rotavirus infection.

BRIEF DESCRIPTION OF THE DRAWING

The figure shows the percent inhibition of rotavirus by lambda-carrageean as compared with kappa- and iota-carrageenan and with dextran sulfate.

BRIEF DESCRIPTION OF THE INVENTION

There is disclosed in the present invention a method for inhibiting infection of animal cells by human rotavirus by exposing the virus to carrageenan. In a preferred embodiment of the present invention, a method is disclosed for inhibiting infection of animal cells by human rotavirus by exposing the virus to λ-carrageenan. A method is also disclosed for treating an individual suffering from rotavirus infection by enteral administration of carrageenan.

DETAILED DESCRIPTION OF THE INVENTION

Two in vitro assays were used to determine the anti-human rotavirus (HRV) activity of sulfated polysaccharides. The first is an infectious focus assay that measures the extent of inhibition of an initial virus infection in single cells. The second is a plaque assay that measures the extent of cell death caused by progeny viruses. The two assays and the results of experiments conducted according to their protocols will be discussed separately.

Experiment 1

Infectious Focus Assay-Inhibition of Initial HRV Infection in Single Cells

An assay using a similar methodology to that used in the present invention appears in Gerna et al. "Immunoperoxidase Technique for Rapid Human Cytomegalovirus Identification", *Archives of Virology*, 50: 311–321, 1984.
Materials and Methods Cells and Viruses: Human Rotavirus serotype Wa was obtained from Dr. Linda Saif (Ohio Agricultural Research and Development Center, Wooster, Ohio). MA 104 cells, derived from fetal African Green Monkey kidney cells, were obtained from Bio Whittaker (Walkersville, Md.). The use of MA 104 cells in HRV neutralization assays has been described in Kitammoto et al., "Comparative Growth of Different Rotavirus Strains in Differentiated Cells (MA104, HepG2, and CaCo-2)", Virology, 184: 729–737, 1991.

MA 104 cells were cultured in Basal Medium Eagle (BME) (Bio Whittaker, Walkersville, Md.) supplemented with 10% Fetal Bovine Serum (FBS) (Hyclone, Logan, Utah). Cells were routinely subcultured in 75 cm² flasks (Costar, Cambridge, Mass.) using Trypsin-EDTA (0.25% trypsin, 1 mM EDTA (ethylenediaminetetraacetic acid) (Gibco Grand Island Biological Co., Grand Island, N.Y.) or Trypsin-Versene 0.5% trypsin, 1 mM EDTA) (Bio Whittaker) to detach cells.

Cells utilized in the HRV infectious focus assay were seeded into 96-well plates (Costar) at a density of 10,000 cells per well in fibronectin coated plates. The cells were maintained at 37° C. in a 95% air:5% $CO_2$ atmosphere humidified incubator for 3–4 days until a confluent monolayer suitable for HRV studies was obtained.

Plates were washed three times with 150 µl diluent medium (BME, 2 mM L-glutamine (Gibco), 25 µg/ml gentamicin sulfate (Gibco), and penicillin-streptomycin (Sigma, St. Louis, Mo.) to remove residual serum proteins before adding HRV. 50 µl diluent medium was added to each well and the plates were maintained at 37° C. until ready for use.

HRV Activation: HRV was activated with trypsin to achieve optimum infectivity. 0.25 ml of 50 IU/ml trypsin (Sigma) in phosphate buffered saline (PBS) was added to 1 ml of HRV stock, mixed well and incubated at 37° C. for 30 minutes. 1 ml of the virus was then diluted with 7 ml of diluent medium to achieve a 1:10 dilution of the original virus stock. 1 ml of the 1:10 dilution was added to 24 ml of diluent medium to obtain a 1:250 dilution, twice the final desired virus concentration.

Preparation of carrageenans: Carrageenans for these studies were initially prepared by adding each carrageenan at a final concentration of 3 mg/ml to 8 ounce glass containers containing phosphate buffered saline (0.017 M $KH_2PO_4$, 1.5 M NaCl at pH 7.4). Samples were hand shaken and hydrated for a minimum of 24 hours at 2°–8° C. Carrageenan prepared in this way was not completely dissolved or dispersed. Therefore, a sample sterilization step was added to the procedure. Samples of carrageenan were retorted using a Steritort continuous sterilizer simulator (FMC, Madera, Calif.) at a minimum product temperature of 255° F. and an F. greater than or equal to 6. The Steritort is a batch retort with a preheat cycle with gradient water, a saturated steam cook cycle, and a cool cycle using gradient water. Agitation was continuous during all cycles. Carrageenans prepared in this manner were used in all experiments described below.

Test agent preparation: Each concentration of test agent was diluted to 2X the final concentration in MA 104 diluent medium. Typically 200 µl of test agent was mixed with 200 µl of virus and preincubated for 60 minutes at room temperature to allow the test agents to react with HRV. Cell controls were prepared by using diluent medium without virus. Bovine anti-HRV immunoglobulin served as a positive anti-vital control and bovine serum albumin was a negative control.

HRV and Cell Incubation: 100 µl of test agent+virus was added to each well and mixed with 50 µl of medium. The plate was then incubated for 12–14 hours at 37° C. in a 5% $CO_2$ :95% air atmosphere to allow the virus to replicate within infected cells. Incubation for longer than 14 hours would have resulted in infection of surrounding MA 104 cells by progeny virus.

Fixation and Staining of MA 104 Monolayers: After incubation, plates were washed twice with 150 µl of PBS and once with 150 µl of 70% ethanol at a temperature between 2° and 8° C. 95 µl of the 70% ethanol was removed and 190 µl of absolute ethanol (2°–8° C.) was added to each well. Plates were then placed in the refrigerator for 18–24 hours. The alcohol was removed using a multichannel pipettor, and 150 µl PBS supplemented with 0.05% chick egg albumin (PBS-CEA) (Sigma) was added to each well to block nonspecific binding of antibody. After removing the PBS-CEA from the MA 104 monolayer, 200 µl of bovine anti-HRV antibody diluted 1:2500 was added to each well. Plates were covered and incubated for 30 minutes at room temperature. The HRV antibody was then removed and the plates were washed 3 times with PBS-CEA at 150 µl per well per wash. 200 µl peroxidase conjugated with rabbit anti-bovine IgG at 1:2000 dilution was added to each well and incubated 30 minutes at room temperature. Each plate was then washed 3 times with 150 µl PBS-CEA to remove unbound conjugate. 100 µl of diaminobenzidine substrate (Sigma) was added to each well and incubated for 20 minutes. After incubation the plates were washed twice with PBS-CEA followed by 2 washes with distilled water to remove unbound peroxidase conjugate.

Enumeration of infected cells: Plates were rehydrated by the addition of water (150–200 µl/well) and examined by light microscopy (100×magnification). HRV infected cells characteristically appeared brown with granular cytoplasmic regions. Stained and infected cells were counted within a uniform area, a vertical strip through the center of each well representing approximately 20% of the area of the well, using a 10 mm ocular grid for orientation.

Calculations: Each sample dilution was tested in triplicate and the average number of infected cells was compared with the number in control wells that contained virus but no test agent. Results were presented as percent inhibition.

Results

Several different types of polysaccharides were tested in the focus assay system for their anti-HRV activity. Not all polysaccharides demonstrated activity. The polysaccharides inulin and carboxymethyl cellulose were tested at concentrations up to 100 µg/ml. Inulin, which is composed of D-fructose and D-glucose, showed no anti-HRV activity. Neither did carboxymethyl cellulose. Dextran sulfate, a polysaccharide composed of a glucose backbone with each glucose containing up to three sulfate groups demonstrated minimal anti-HRV activity. Table 1 shows that 100 µg/ml of dextran sulfate were required to obtain 50% inhibition of HRV activity.

Three types of carrageenans were tested for their anti-HRV activity. Iota- and kappa-carrageenans contain a backbone of β-D-galactose-4-sulfate and 3,6-anhydro-α-D-galactose subunits. They differ at the 2 position of 3,6-anhydro-α-D-galactose where κ-carrageenan has a hydrogen and ι-carrageenan is sulfated. ι- and κ-carrageenans showed minimal anti-HRV activity at concentrations up to 100 µg/ml. Unexpectedly, λ-carrageenan demonstrated significant anti-HRV activity at low concentrations. 50% inhibition of HRV activity was seen at 0.3 µg/ml ($IC_{50}$=0.3 µg/ml). λ-carrageenan is structurally similar to κ- and ι- carrageenan, consisting of a backbone of β-D-galactose-2-sulfate and 2,6-disulfate-α-D-galactose.

Results of the infectious focus assay are shown in Table 1.

Experiment 2

Plaque Assay-Cell Death Caused by Progeny Viruses

An assay using a methodology similar to that used in the present invention was described in Kitammoto et al.

Materials and Method

Cells and Virus: MA 104 cells were obtained from Dr. Richard Ward (James N. Gamble Institute of Medical Research, Cincinnati, Ohio). Virus was obtained as described for the focus assay. MA 104 cells used in the plaque assays were seeded into Costar 6-well plates and grown to confluence in growth medium. Cells were washed twice in serum free MEM (Minimal Essential Medium) (Sigma) before the virus was added.

HRV activation: HRV was activated as described for the focus assay. The activated virus was diluted to a 1:5,000 dilution which was twice the final virus concentration used to infect the cell monolayer. The test agent was then diluted to twice the final testing concentration in DME serum free medium.

Test agent preparation: Test agent was prepared as described for the focus assay.

HRV and cell incubation: 0.5 ml of virus+test agent was placed in the appropriate well of the 6-well plate for 1 hour to give the virus time to adsorb onto the cells. Every 15 minutes the plates were rocked to keep the cell monolayers from drying. Agarose (SeaKem) (FMC Bioproducts, Rockland, Me.) was prepared at a concentration of 0.4 g/ml in distilled water and autoclaved. After cooling to 44° C., the agarose was mixed with an equal amount of 2× serum-free medium containing 0.25 units/ml trypsin. Inoculated cells containing virus and test agents were immediately overlaid with 5 ml agar. Plates were maintained at 37° C. in a 95% air:5% $CO_2$ atmosphere humidified incubator until plaques were observed.

Staining MA 104 monolayers: After 3 or 4 days incubation the agar was removed from each plate and crystal violet stain (0.4%, Becton Dickinson, Cockeysville, Md.) was added to each well. The wells were stained for a minimum of 5 minutes and the plates thoroughly washed with tap water, inverted, and air dried.

Enumeration of plaques: HRV plaques were quantitated by estimating the percent reduction in plaques in wells containing test agent compared to controls where only virus but no test agent was present. Typically, there were 40–50 plaques in control wells.

Results

In the plaque reduction assay λ-carrageenan showed anti-viral activity as it had in the infectious focus assay. As shown in Table 1, a 50% reduction in plaque number was achieved at a λ-carrageenan concentration of 6 µg/ml. These results demonstrate the potent anti-HRV activity of λ-carrageenan. Only those test agents that had shown evidence of anti-viral potency in the infectious focus assay were retested in the plaque reduction assay. Therefore, inulin, carboxymethyl cellulose, ι-carrageenan, and κ-carrageenan were not tested in the plaque reduction assay. Bovine anti-HRV immunoglobulin was used as a positive control and bovine serum albumin as a negative control in the plaque reduction assay as in the infectious focus assay.

TABLE 1

Test Results Showing Ability of Test Agents to Inhibit Rotavirus Infection of MA 104 Cells

| TEST AGENT | INFECTIOUS FOCUS ASSAY $IC_{50}$ in µg/ml | PLAQUE REDUCTION ASSAY $IC_{50}$ in µg/ml |
|---|---|---|
| Inulin | >100 | not tested |
| Carboxymethylcellulose | >100 | not tested |
| Dextran sulfate | 50 | >30* |
| ι-carrageenan | >100 | not tested |
| κ-carrageenan | >100 | not tested |
| λ-carrageenan | 0.3 | 6 |
| Bovine anti-HRV immunoglobulin | 0.08 | 0.14 |
| Bovine serum albumin | >3,000 | >3,000 |

*Toxic at ≧100 µg/ml

The studies presented here demonstrate that lambda-carrageenan inhibited rotavirus infection of animal cells as measured in two different assays. Dextran sulfate was efficacious to a lesser extent. The other tested agents, including the two other carrageenans, did not exhibit anti-rotaviral activity as measured by ability to inhibit initial infection of a cell by the virus. Lambda-carrageenan inhibited both initial infection and infection followed by cell death caused by progeny viruses. Experimental results are shown in the graph which constitutes the sole drawing.

This result was both unexpected and non-obvious to one skilled in the art. The efficacy of $\lambda$-carrageenan, but not $\iota$- or $\kappa$-carrageenan, was contrary to the findings of the prior art in several respects: (1) the prior art described the inhibitory properties of carrageenan with respect to enveloped viruses, such as retroviruses, and even reported carrageenan to be ineffective against non-enveloped viruses (De Clerq); (2) iota- and lambda- carrageenan were found to be equally effective against a hepatitis virus (Girond).

Use of Sulfated Polysaccharides in Treating Rotavirus Infections

Previous research on carrageenan has shown it to be safe with few, if any, side-effects. It is approved by the U.S. Food and Drug Administration for use in foods and cosmetics, and is not absorbed by the epithelium of the gastrointestinal tract. Carrageenan is a fairly strong buffer, and in formulations containing carrageenan the pH can be adjusted without the use of additional buffer. Carrageenan can be ingested enterally prior to and during infection with rotavirus and is, thus useful in the prevention and treatment of rotavirus caused diarrhea.

The sulfated polysaccharides of the present invention include, but are not limited to dextran sulfate, lambda-carrageenan, iota-carrageenan, and kappa-carrageenan with lambda-carrageenan the preferred form. Lambda-carrageenan can be added to nutritional substances such as infant formula and such formulations are an aspect of the invention.

What is claimed is:

1. A method of inhibiting the infection of animal or human gastrointestinal epithelial cells by rotavirus comprising contacting said rotavirus with lambda-carrageenan.

2. The method according to claim 1 wherein said step of contacting occurs in vitro.

3. The method according to claim 1 wherein the human is an infant or a child.

4. A method of inhibiting infection of animal cells by rotavirus comprising exposing said virus to lambda-carrageenan.

5. The method of claim 4 wherein the animal is a human and the cells are gastrointestinal epithelia cells.

6. The method of claim 4 wherein said step of exposing occurs in vitro.

7. The method of claim 5 wherein said human is an infant or a child.

* * * * *